(12) United States Patent
Daffer et al.

(10) Patent No.: US 7,406,109 B2
(45) Date of Patent: Jul. 29, 2008

(54) HAND HELD LASER FOR MEDICAL TREATMENT

(75) Inventors: Steven J. Daffer, Edina, MN (US); Zhang X. Song, Beijing (CN)

(73) Assignee: Visibelle Derma Institue, Inc., Bloomington, MN (US)

( * ) Notice: Subject to any disclaimer, the term of this patent is extended or adjusted under 35 U.S.C. 154(b) by 0 days.

(21) Appl. No.: 11/712,208

(22) Filed: Feb. 28, 2007

(65) Prior Publication Data

US 2007/0250137 A1    Oct. 25, 2007

Related U.S. Application Data

(60) Provisional application No. 60/778,182, filed on Mar. 1, 2006.

(51) Int. Cl.
*H01S 3/04* (2006.01)
*H01S 3/042* (2006.01)
*A61B 18/20* (2006.01)

(52) U.S. Cl. .............................. 372/34; 372/35; 372/36; 372/70; 606/10; 606/13; 607/89

(58) Field of Classification Search ............. 372/34–36, 372/69, 70; 606/3–5, 8–13; 607/88, 89
See application file for complete search history.

(56) References Cited

U.S. PATENT DOCUMENTS

| | | | |
|---|---|---|---|
| 3,599,113 A * | 8/1971 | Cremosnik .................... | 372/35 |
| 3,702,976 A | 11/1972 | Young ....................... | 331/94.5 |
| 3,821,510 A | 6/1974 | Muncheryan ............ | 219/121 L |
| 3,979,696 A | 9/1976 | Buchman ................. | 331/94.5 P |
| 4,096,450 A * | 6/1978 | Hill et al. ...................... | 372/34 |
| 4,232,276 A | 11/1980 | Iwata .................... | 331/94.5 D |
| 4,517,974 A | 5/1985 | Tanner .................... | 128/303.1 |
| 4,608,980 A | 9/1986 | Aihara .................... | 128/303.1 |
| 4,637,028 A * | 1/1987 | Kahan ......................... | 372/34 |
| 4,644,550 A | 2/1987 | Cséry et al. .................. | 372/40 |
| 4,671,273 A | 6/1987 | Lindsey ................... | 128/303.1 |
| 4,808,789 A | 2/1989 | Muncheryan ............ | 219/121.6 |
| 4,826,431 A | 5/1989 | Fujimura et al. .............. | 433/29 |
| 4,858,243 A | 8/1989 | Bar-Joseph .................. | 372/72 |
| 4,887,270 A * | 12/1989 | Austin ......................... | 372/22 |
| 5,481,556 A * | 1/1996 | Daikuzono .................. | 372/34 |
| 5,548,604 A * | 8/1996 | Toepel ......................... | 372/35 |

(Continued)

OTHER PUBLICATIONS

International Search Report and Written Opinion of Application No. PCT/US07/05318, Mar. 1, 2007.

*Primary Examiner*—Ahmed M Farah
(74) *Attorney, Agent, or Firm*—Westman, Champlin & Kelly, P.A.

(57) ABSTRACT

A hand held laser for treating a skin condition includes a housing comprising a first end, a second end and a cavity therein wherein the cavity includes a substantially light reflective surface and wherein the housing comprises at least one fin extending from an exterior surface of the housing. The laser includes a flash lamp having a first axis and being retained within the cavity in a first selected position and a laser rod having a second axis and being retained within the cavity in a second selected position and wherein the first axis and the second axis are substantially parallel to each other, wherein as the flash lamp is pumped the laser rod produces a laser beam for treating the skin condition.

20 Claims, 4 Drawing Sheets

U.S. PATENT DOCUMENTS

| | | |
|---|---|---|
| 5,588,952 A | 12/1996 | Dandolu |
| 6,039,729 A | 3/2000 | Durville et al. |
| 6,251,102 B1 * | 6/2001 | Gruzdev et al. ............... 606/10 |
| 6,813,289 B2 * | 11/2004 | Gruzdev et al. ............... 372/34 |
| 2005/0085802 A1 | 4/2005 | Gruzdev et al. |
| 2005/0147140 A1 | 7/2005 | Aiken ......................... 372/35 |

* cited by examiner

HAND HELD LASER FOR MEDICAL TREATMENT

CROSS REFERENCE TO RELATED APPLICATION

The present application is based on and claims the benefit of U.S. provisional patent application Ser. No. 60/778,182, filed Mar. 1, 2006, the content of which is hereby incorporated by reference in its entirety.

FIELD OF THE INVENTION

The present invention relates to a laser for use in medical treatments. More particularly, the present invention relates to hand held laser for use in medical treatments.

BACKGROUND OF THE INVENTION

Lasers are being used more frequently in medical treatments to reduce blemishes on a patient's skin. Lasers are useful in removing port wine stains, scars and wrinkles from a patient's skin to improve the patient's appearance. Lasers are also useful in removing unwanted tattoos.

Many of the laser treatments require the laser to be mobile to treat the skin blemish. To accommodate the need to for the laser to be mobile, the size of the lasers are being reduced such that the laser can be housed in a hand held housing. However, the laser must supply enough energy to complete the selected procedure. The small size of the laser coupled with the energy delivery requirements has caused the lasers to have a tendency to heat up over time with use, and require the laser to be shut down to cool to a selected temperature.

Typically, water or another cooling fluid is utilized to remove the heat that is generated as the laser is utilized. However, because of the mobility and energy requirements of the laser, a circulating coolant may not remove a sufficient amount of heat to allow the laser to run continuously for an extended period of time without heating to excessive temperatures.

SUMMARY OF THE INVENTION

The present invention includes a hand held laser for treating a skin condition having a housing comprising a first end, a second end and a cavity therein wherein the cavity includes a substantially light reflective surface and wherein the housing comprises at least one fin extending from an exterior surface of the housing. The laser includes a flash lamp having a first axis and being retained within the cavity in a first selected position and a laser rod having a second axis and being retained within the cavity in a second selected position and wherein the first axis and the second axis are substantially parallel to each other, wherein as the flash lamp is pumped the laser rod produces a laser beam for treating the skin condition.

DETAILED DESCRIPTION

Figure 1:
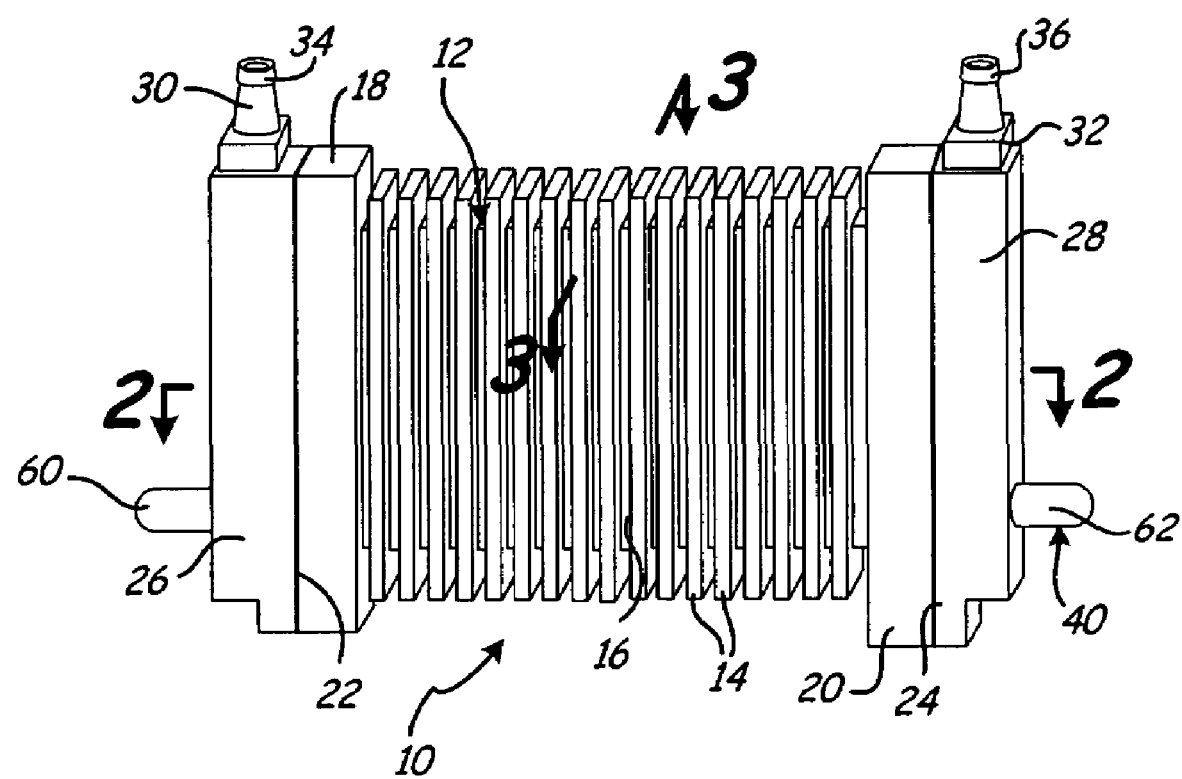
FIG. 1 is a perspective view of the hand-held laser of the present invention.

A hand-held laser of the present invention is generally illustrated in FIG. 1 at 10. The hand-held laser 10 includes a housing 12 with a plurality of fins 14 extending from an exterior surface 16 and about a perimeter of the housing 12. The plurality of fins 14 increase the surface area of the external surface 16 of the housing 12 which increases the rate at which heat is transferred from the laser 10 to the atmosphere proximate the laser 10.

The housing 12 typically includes seventeen uniformly spaced fins 14 extending around the perimeter of the housing 12. However, a housing 12 with one or more fins 14 is contemplated that may or may not extend around the entire perimeter of the housing 12.

The housing 12 is typically constructed from stainless steel. Stainless steel is a desirable material of construction due to its strength, durability, resistance to corrosion, ability to reflect light beams and high heat capacity. However, other materials of construction of the housing 12 are also contemplated including, but not limited to gold, silver and titanium.

The housing 12 is typically of a unitary construction. However a housing 12 with two or more components secured together are also contemplated.

Figure 4:
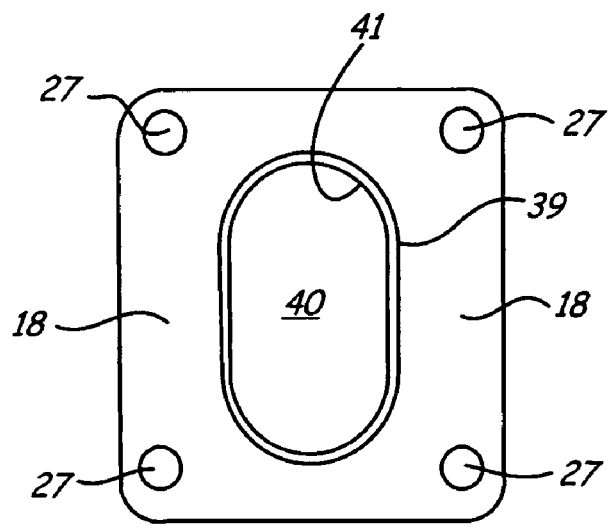
FIG. 4 is a left side view of the main body of the laser of the present invention.
Figure 5:
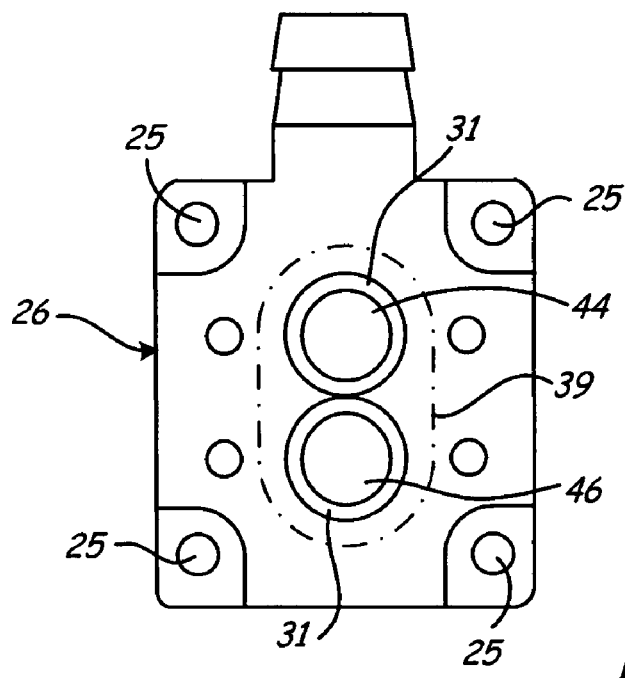
FIG. 5 is a left side view of the laser of the present invention.

Left and right end caps 26, 28 are attached to the left and right ends 18, 20, respectively, of the housing 12. The left and right end caps 26, 28 are typically attached to the left and right ends 18, 20 of the housing 12 with threaded engagements of bolts 25 with threaded bores 27 proximate the corners of the left and right end caps 26, 28 as illustrated in FIGS. 4 and 5. The engagements of the left and right end caps 26, 28 with the left and right ends 18, 20 of the housing 12 typically form seals at seams 22, 24, respectively. However, it is also contemplated to utilize a gasket between the left and right end caps 26, 28 and the left and right ends 18, 20, respectively, to form the seals.

A cooling medium, typically water, is supplied to the laser 10 through an inlet 30, typically attached to the left end cap 26. The cooling medium exits the laser 10 through an outlet 32, typically attached to the right end cap 28. The inlet 30 and the outlet 32 both have at least one ridge 34, 36, respectively, around the perimeter for securing tubes (not shown) thereto.

Figure 2:
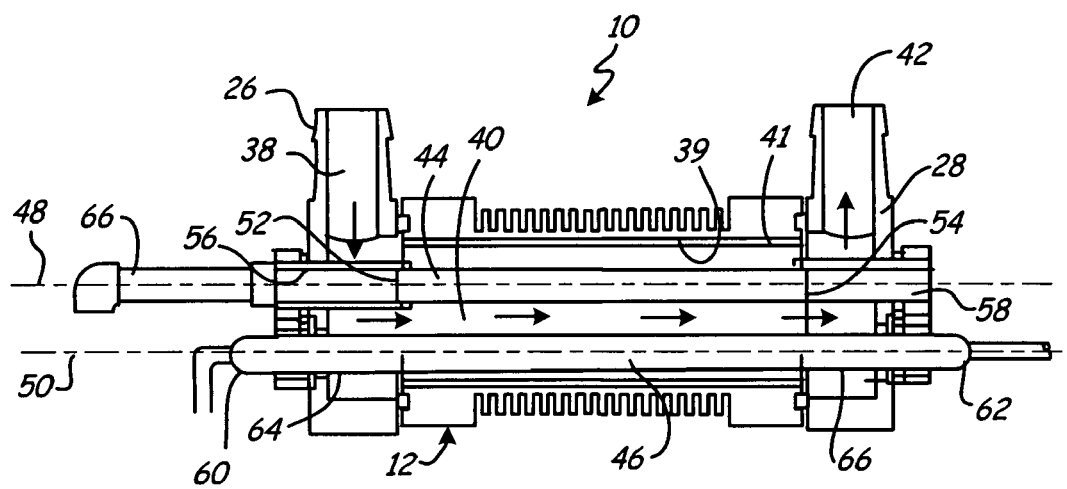
FIG. 2 is a sectional view of the hand-held laser of the present invention along section line 2-2 in FIG. 1.

Referring to FIG. 2, the cooling medium passes through a left passage 38 in the left end cap 26 and into a cavity 40 in the housing 12 where the cooling medium fills the cavity 40. A glass tube 41 is positioned into the cavity 40 wherein the glass tube 41 is adjacent a cavity surface 39. The glass tube 41 prevents corrosion to the cavity surface 39 which can be caused by contact between the cooling medium and the surface 39 defining the cavity 40 over time.

The cooling medium exits the right end 24 of the housing 12 and passes through a right passage 42 in the right end cap 28 and out of the laser 10 through the outlet 32. Depending upon the configuration of the laser 10, the flow of the cooling medium may be reversed.

A flash lamp 44 and a laser rod 46 are positioned in selected positions within the cavity 40 in a substantially parallel configuration. Ends 52, 54 of the flash lamp 44 extend beyond the left and right ends 22, 24 of the housing 12 and are positioned within through bores 56, 58 in the left and right end caps 26, 28, respectively. Positioning the ends 52, 54 of the flash lamp 44 within the through bores 56, 58 secures the flash lamp 44 in a selected position within the cavity 40. Referring to FIG. 5, gaskets such as O-rings 31 are typically utilized to form a seal between the end caps 26, 28 and the ends 52, 54 of the flash lamp 44 to retain the liquid coolant within the cavity 40.

Ends 60, 62 of the laser rod 46 are positioned through bores 64, 66 in the left and right end caps 26, 28, respectively such that the laser rod ends 60, 62 extend beyond the end caps 26, 28. Positioning the ends 60, 62 within the through bores 64, 66 secures the laser rod 46 in a selected position within the cavity 40 such that the axis 48 of the flash lamp 44 is substantially parallel to an axis 50 of the laser rod 46. Gaskets such as 0-rings 31 are utilized to form a seal between the end caps 26, 28 and the ends 60, 62 of the laser rod 46 to retain the liquid coolant within the cavity 40.

The through bore 66 provides an opening through which a laser beam is directed from the hand held laser 10. A diameter of the laser beam is equivalent to the diameter of the laser rod 46 which is typically about 5 mm. However the diameter of the beam, as well as a shape of the beam, can be varied by manipulating a collimator (not shown) positioned beyond the through bore 66. The collimator is capable of reducing the diameter of the beam to less than one millimeter. It is also contemplated that the beam be separated into multiple beams through beam splitting techniques.

The laser rod 46 is typically an Er:YAG laser rod that is designed to deliver between about 1.2 J/cm$^2$ and about 1.5 J/cm$^2$ at a frequency of about 2940 nm. The laser rod 46 is typically about 5 mm in diameter and about 80 mm in length. However, other laser mediums besides an Er:YAG laser are also contemplated as well as a laser that delivers a different amount of energy at a different frequency. It is also contemplated to utilize a laser rod 46 having a diameter and length different than a 5 mm diameter and an 80 mm length, provided the laser rod 46 is of a size that can be utilized as a hand-held laser 10.

Figure 6:
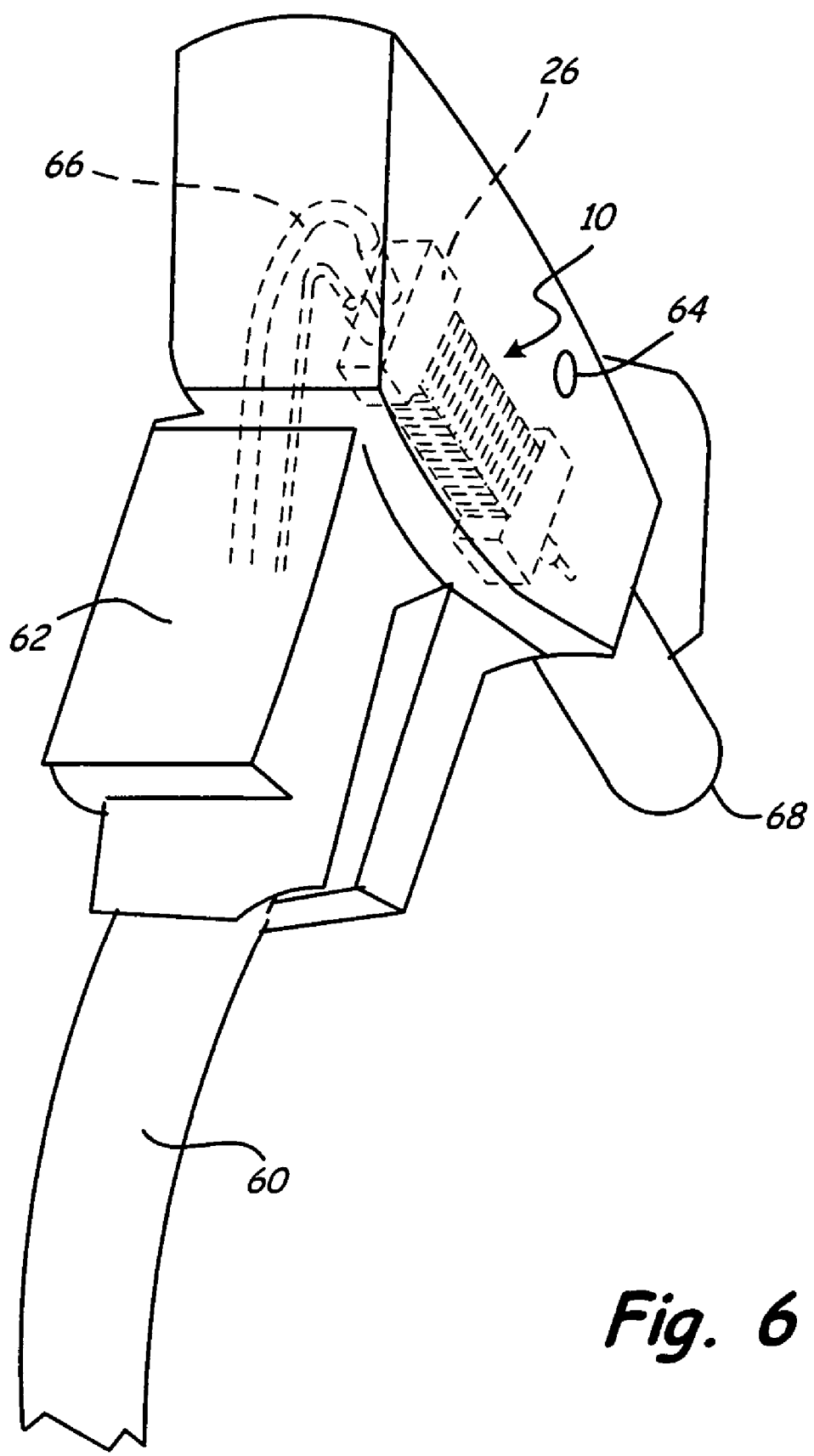
FIG. 6 is a perspective view of a casing containing the laser of the present invention.

Referring to FIG. 6, power is supplied to the flash lamp 44 through an umbilical cord 60 that also supplies the cooling medium and other utilities including electricity and optionally a compressed coolant gas that may be required for the laser 10 to properly function. Typically, the umbilical cord 60 attaches to the left end cap 26. However, the umbilical cord 60 can also be attached to the housing 12 as well as the right end cap 28 to supply the necessary utilities to the laser 10.

Power is supplied through a connection 66 to the flash lamp 44 typically in intervals in rapid succession, otherwise referred to as "pumping". As the flash lamp 44 is pumped, the flash lamp 44 supplies energy to the laser rod 46 in the form of light energy. The energized laser rod 46 then supplies the laser beam through an aperture 68 in the casing 62 that is utilized in the medical treatment.

As the flash lamp 44 is pumped and the laser rod 46 is energized, a significant amount of heat is generated. Some of the heat is removed from the laser 10 by circulating the cooling medium through the cavity 40. As the cooling medium passes through the cavity 40, the cooling medium contacts the laser rod 46, the flash lamp 44 and the glass liner 41 to remove heat from the laser 10. The cooling medium typically flows in a direction of arrows illustrated in FIG. 2 within the cavity 40 substantially along the axis 48, 50 of the flash lamp 44 and the laser rod 46 while removing heat from the laser 10.

Heat is also removed from the laser 10 by transferring heat into the atmosphere through the exterior surface 16 of the housing 12 that includes the plurality of fins 14 which increase the surface area of the exterior surface 16. Typically, the laser 10 will be contained within an enclosed casing 62 where a forced gaseous cooling medium, typically air, is supplied to the casing 62 through the umbilical cord. The gaseous cooling medium passes over the outer surface of the laser 10 the plurality of fins 14 to remove heat from the housing 12. The casing 62 also typically includes an outlet 64 for the forced gaseous cooling medium to exit the casing.

Heat is also removed from the laser through the end caps 26, 28 which are in thermal contact with the housing 12. Heat is dissipated through the end caps 26, 28 and into the surrounding atmosphere, typically the forced gaseous medium, to aid in cooling the laser 10. The end caps 26, 28 are typically constructed of aluminum to minimize the weight of the laser 12. However, other materials of construction of the end caps 26, 28 are also contemplated.

Figure 3:
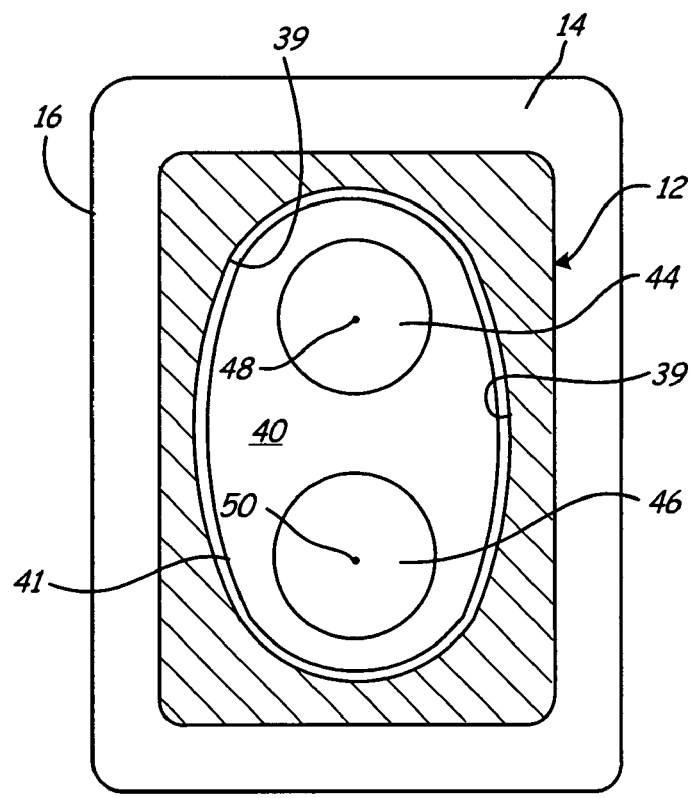
FIG. 3 is a sectional view along section line 3-3 in FIG. 1.

Referring to FIGS. 3-5, the cavity 40 has a substantially elliptical cross-section that is defined by the surface 39 which increases the efficiency of the laser 10. The elliptical configuration redirects the light energy from the flash lamp 44 into the laser rod 46 more efficiently than other configurations of the cavity 40, such as a circular cross-sectional cavity. The elliptical surface 39 is typically coated with a reflective material, typically gold, to increase the amount of light energy that redirected into the laser rod 46. However other reflective materials such as, but not limited to, silver and titanium are also contemplated. Other cross-sectional configurations of the cavity 40 that are less efficient than an elliptical cross-sectional cavity 40 are also contemplated, including but not limited to including a circular cross-section.

Although the present invention has been described with reference to preferred embodiments, workers skilled in the art will recognize that changes may be made in form and detail without departing from the spirit and scope of the invention.

What is claimed is:

1. A hand held laser configured to be grabbed by hand and moved with manual force for treating a skin condition, the laser comprising:
    a housing comprising a first end, a second end and a cavity therein wherein the cavity includes a substantially light reflective surface and wherein the housing comprises at least one fin extending from an exterior surface of the housing;
    a flash lamp having a first axis and being retained within the cavity in a first selected position;
    a laser rod having a second axis and being retained within the cavity in a second selected position and wherein the first axis and the second axis are substantially parallel to each other, wherein as the flash lamp is pumped the laser rod produces a laser beam for treating the skin condition;
    a stream of cooling liquid circulating within the housing and contacting the flash lamp and laser rod to remove heat that is generated during use; and
    a stream of cooling gas contacting the housing including the at least one fin such that the cooling gas removes heat generated during use wherein simultaneously removing heat with both the cooling liquid and the cooling gas allows the hand held laser to be continuously used for an extended period of time without having to be deenergized to allow the device to cool.

2. The laser of claim 1 and further comprising:
    a first end cap attached to the first end of the housing and wherein the first end cap includes a first flash lamp aperture and a first laser rod aperture for securing first ends of the flash lamp and the laser rod; and
    a second end cap attached to the second end of the housing and wherein the second end cap includes a second flash lamp aperture and a second laser rod aperture for securing second ends of the flash lamp and the laser rod.

3. The laser of claim 2 and wherein the first end cap and the second end cap form seals with the first and second ends of the housing.

4. The laser of claim 2 and further comprising:
an inlet into the cavity through the first end cap;
an outlet from the cavity though the second end cap; and
wherein the cooling liquid enters the cavity through the inlet and flows through the cavity substantially along the axes of the flash lamp and the laser rod and exits the laser through the outlet to remove heat generated through use of the laser.

5. The laser of claim 4 and wherein the cooling liquid comprises water.

6. The laser of claim 1 and wherein the housing comprises a plurality of fins about a perimeter of the housing.

7. The laser of claim 1 and wherein the housing is of a unitary construction.

8. The laser of claim 1 and wherein the housing comprises stainless steel.

9. The laser of claim 1 and wherein the housing is contained within a casing having an aperture for providing the laser for treating the skin condition.

10. The laser of claim 9 and wherein a gaseous medium is forced into the casing and into contact with the housing having the at least the one fin to remove heat from the laser and wherein the housing contains an exit for the heated gaseous medium.

11. The laser of claim 1 and further comprising an umbilical cord that supplies at least power to energize the laser.

12. A hand held laser configured to be grabbed by hand and moved with manual force for treating a skin condition, the laser comprising:
a housing comprising a first end, a second end and a cavity therein wherein the cavity includes a substantially light reflective surface and wherein the housing comprises at least one fin extending from an exterior surface of the housing;
a flash lamp having a first axis and being retained within the cavity in a first selected position;
a laser rod having a second axis and being retained within the cavity in a second selected position and wherein the first axis and the second axis are substantially parallel to each other, wherein as the flash lamp is pumped the laser rod produces a laser beam for treating the skin condition;
a casing having a sufficient size to contain the housing and wherein the housing provides a surface for gripping and directing the laser;
a stream of cooling liquid circulating within the housing and contacting the flash lamp and laser rod to remove heat that is generated during use; and
a stream of cooling gas contacting the housing including the at least one fin such that the cooling gas removes heat generated during use wherein simultaneously removing heat with both the cooling liquid and the cooling gas allows the hand held laser to be continuously used for an extended period of time without having to be deenergized to allow the device to cool.

13. The laser of claim 12 and further comprising:
a first end cap attached to the first end of the housing and wherein the first end cap includes a first flash lamp aperture and a first laser rod aperture for securing first ends of the flash lamp and the laser rod; and
a second end cap attached to the second end of the housing and wherein the second end cap includes a second flash lamp aperture and a second laser rod aperture for securing second ends of the flash lamp and the laser rod.

14. The laser of claim 13 and wherein the first end cap and the second end cap form seals with the first and second ends of the housing.

15. The laser of claim 14 and further comprising:
an inlet into the cavity through the first end cap;
an outlet from the cavity though the second end cap; and
wherein the cooling liquid enters the cavity through the inlet and flows through the cavity substantially along the axes of the flash lamp and the laser rod and exits the laser through the outlet to remove heat generated through use of the laser.

16. The laser of claim 15 and wherein the cooling liquid comprises water.

17. The laser of claim 12 and wherein the housing comprises a plurality of fins substantially about a perimeter of the housing.

18. The laser of claim 12 and wherein the housing is of a unitary construction.

19. The laser of claim 12 and wherein a gaseous medium is forced into the casing and into contact with the housing having the at least the one fin to remove heat from the laser and wherein the housing contains an exit for the heated gaseous medium.

20. The laser of claim 12 and further comprising an umbilical cord that supplies at least power to energize the laser.

* * * * *